United States Patent
Rahbar-Dehghan (10) Patent No.: US 8,342,710 B2
(45) Date of Patent: Jan. 1, 2013

(54) LOUPE AND LIGHTING ASSEMBLY FOR CAMERA SENSOR DUST DETECTION

(75) Inventor: Fariborz Rahbar-Dehghan, Canmore (CA)

(73) Assignee: 1317442 Alberta Ltd., Canmore, Alberta (CA)

(*) Notice: Subject to any disclaimer, the term of this patent is extended or adjusted under 35 U.S.C. 154(b) by 470 days.

(21) Appl. No.: 12/663,991

(22) PCT Filed: Jun. 5, 2008

(86) PCT No.: PCT/CA2008/001068
§ 371 (c)(1),
(2), (4) Date: Dec. 10, 2009

(87) PCT Pub. No.: WO2008/151414
PCT Pub. Date: Dec. 18, 2008

(65) Prior Publication Data
US 2010/0188841 A1  Jul. 29, 2010

Related U.S. Application Data

(60) Provisional application No. 60/934,263, filed on Jun. 12, 2007.

(51) Int. Cl.
*F21S 4/00* (2006.01)
*F21V 11/00* (2006.01)
(52) U.S. Cl. .......... 362/249.02; 362/236; 362/234; 362/109
(58) Field of Classification Search ........... 362/249.02, 362/230, 231, 109, 157, 138, 139, 234, 236, 362/253, 11, 249.03–249.06, 800; 396/429, 396/199, 531
See application file for complete search history.

(56) References Cited

U.S. PATENT DOCUMENTS

| | | | | |
|---|---|---|---|---|
| 3,908,119 | A * | 9/1975 | Zeytoonian | 362/140 |
| 5,038,258 | A | 8/1991 | Koch et al. | |
| 6,322,226 | B1 * | 11/2001 | Dickson | 362/33 |
| 6,739,738 | B1 * | 5/2004 | Smith | 362/317 |
| 7,430,311 | B2 * | 9/2008 | Sones et al. | 382/143 |
| 7,625,100 | B2 * | 12/2009 | Sones et al. | 362/249.02 |
| 7,805,070 | B2 * | 9/2010 | Parkola et al. | 396/429 |
| 2007/0057210 | A1 | 3/2007 | Caldwell | |

FOREIGN PATENT DOCUMENTS

CA  2282498  8/1999
(Continued)

*Primary Examiner* — Bao Q Truong
(74) *Attorney, Agent, or Firm* — Fraser Clemens Martin & Miller LLC; J. Douglas Miller (57) ABSTRACT

A loupe and lighting assembly for enhancing detection of dust particles on the optical sensor of a digital camera. The assembly is made of a cylindroid hollow-centered main frame body, into which is fixed a loupe lens. A battery housing is joined to the body in order to supply electrical power to a LED array. The LED array is made from a plurality of LED diodes mounted peripherally and around the inside of the cylindroid body, being tilted at an acute angle from the axis orthogonal to the plane of the cylindroid body so that all diodes axially converge toward a single focal point, at a certain distance from the main frame body. The dust particles scattered upon the sensor become clearly visible to an observer looking through the assembly when the dust particles location coincide with the LED common focal point.

10 Claims, 10 Drawing Sheets

FOREIGN PATENT DOCUMENTS

| | | |
|---|---|---|
| CA | 2 333 585 | 12/1999 |
| CA | 2 467 624 | 5/2004 |
| CA | 2 234 515 | 8/2006 |
| CN | 2779215 Y | 5/2006 |
| JP | 2005024905 A | 1/2005 |
| WO | WO9962263 | 12/1999 |
| WO | WO 2008/039309 A2 | 4/2008 |

* cited by examiner

LOUPE AND LIGHTING ASSEMBLY FOR CAMERA SENSOR DUST DETECTION

CROSS-REFERENCE DATA

The present application claims Paris convention priority based upon U.S. provisional patent application No. 60/934,263 filed Jun. 12, 2007.

FIELD OF THE INVENTION

The present invention relates to an assembly of a loupe and lighting means that can be used to enhance detection of dust particles on the sensor of digital cameras.

BACKGROUND OF THE INVENTION

Digital cameras comprise a sensor chamber in which is lodged an electronic sensor, such as a charge-coupled device (CCD) sensor or Complementary Metal Oxide Semiconductor (CMOS) sensor, onto which is projected the image of what is seen through the lens of the camera. This sensor can acquire the image projected thereon and convert it into electronic data, which is thereafter forwarded to data processing means provided on the digital camera. The data processing means then converts this electronic data into an image file of known format, such as in JPEG, TIFF or RAW formats, stored thereafter on the memory card of the camera. Of course, this sensor must remain as clean as possible, since impurities deposited thereon can undesirably alter the final image acquired by the camera.

It is inevitable that during normal use of a digital camera, its sensor will become exposed to the atmosphere and its airborne impurities, such as minute airborne dust particles. More particularly, on digital cameras having interchangeable lenses such as digital single-lens reflex (DSLR) cameras, the sensor inevitably becomes exposed to the atmosphere and its impurities whenever the lens is removed from the body of the camera, for example when switching lenses.

Digital camera owners have come up with a number of means to find out if their camera's sensor is covered with contaminants before proceeding with its cleaning. One of them, called the f22 test, consists of shooting pictures while aiming at a lighted backdrop with a uniform background and consistent lighting, while the camera is set on the longest focal length and smallest aperture value. Then, impurities of the sensor surface appear on the photography as blurring spots altering the image. Consequently, this method may require several picture takings and computer application work to bring out the contrast of blur spots on the photography.

It is noted that ordinary magnification without focused light can't help with inspecting the camera sensor surface, since the camera sensor location is deep within the camera frame and ambient light reach this location only minimally. Also, the inspection light can't shine on the sensor directly without causing possibly irreparable damage.

OBJECTS OF THE INVENTION

A first object of this invention is to provide an improved means to find out if the sensor of a digital camera is covered with dust particles.

A second object of this invention is to provide a good characterization of the shape and/or size of the dust particles resting on the surface of a digital camera sensor by lighting it from different angles, instead of only relying on an overlying light source.

SUMMARY OF THE INVENTION

The aforementioned problems are obviated by the present invention which combines the magnification of a loupe and the reflective properties of a configuration of lamps whose rays shine with relatively acute incident angles instead of shining orthogonally to the sensor surface to detect the dust particles remaining on the digital camera sensor surface.

Furthermore, the configuration of lamps preferably comprises an even number of lamps which are strategically disposed to produce a 3 dimensional effect of the particles remaining onto the camera sensor surface, thus enhancing detection and/or characterization of the dust particles. In other words, illumination of an object from an overlying position will end up with a diffuse halo of shade, while illumination at different angles will generate a more realistic form as explained in the configuration herein after. This invention intends to make that task quicker and more users friendly when compared to traditional means of accomplishing the same task like the f22 test, as described above.

The present invention thus relates to a loupe and lighting assembly for enhancing detection of particulate contaminants on a planar surface, said assembly comprising a power source, a main frame body, light emitting means carried by said frame and operatively connected to said power source and a loupe lens also carried by the main frame, said light emitting means having means for generating a 3 dimensional effect over the particulate contaminants on the planar surface, wherein enhanced detection and characterization of the particulate contaminants is achieved.

In one embodiment, the light emitting means consists of a number of LED diodes arrayed peripherally of said main frame body.

Preferably, the means for generating a 3 dimensional effect consists in each LED diode being tilted with a small acute angle from the axis extending orthogonally through the plane of said main frame body, so that said diodes are focused at a common point in space ahead of said assembly.

The shape of said main frame body of said loupe and lighting assembly is selected from the group comprising cylindroid shape and quadrangular shape.

The main frame body could be of cylindroid shape with said LED diodes disposed peripherally and equidistantly within said cylindroid body.

Preferably, the LED diodes acute angle ranges between 30 to 45 degrees, and most preferably about 30 degrees.

In another embodiment, the LED diodes are disposed in first and second transversely spaced adjacent rows inside the cylindroid body, said LED diodes from said first row having a first acute angle and said LED diodes from said second row having a second acute angle different from said first acute angle.

In this latter embodiment, the first acute angle is preferably about 30 degrees and said second acute angle is preferably about 45 degrees.

Each of said first row and said second row may comprise 6 LED diodes peripherally and equidistantly disposed inside said cylindroid main frame body.

The bottom end of said cylindroid main frame body may be shaped and sized complementarily to a digital camera site to abuttingly fit therein.

In one embodiment, the light-emitting diodes are of an even number.

The power source is preferably an electrical battery operatively carried by said main frame body, said battery powering said loupe and lighting assembly and said main frame body comprising a sliding panel which covers said battery and insures said battery stays in place.

The loupe lens could have magnification capacity between 5× and 10×, and preferably between 5× and 7×.

In another embodiment, the electromagnetic spectrum emitted by said LED diodes is selected from the group comprising the ultraviolet range and the infrared range of wavelengths.

In another embodiment, the loupe lens further includes an anti-reflective coating, preferably made of $MgF_2$.

In another embodiment, a manual trigger switch is provided to said main frame body and operatively connected to said power source and to said light emitting means, said trigger switch enabling the user to selectively activate said loupe and lighting assembly only when required and thus preventing unnecessary use of said power source.

The invention also relates to a method of use of a loupe and lighting assembly of the type comprising a battery power source, a main frame body, light emitting means carried by said frame and operatively connected to said power source and a loupe lens also carried by the main frame, said light emitting means having means for generating a 3 dimensional effect over the particulate contaminants on the planar surface, wherein enhanced detection and characterization of said particulate contaminants is achieved, said method comprising the following steps:
 a) placing camera face up on the table, with the removable lens taken off;
 b) bringing loupe and lighting assembly in register with the lens socket site;
 c) powering the battery power source; and
 d) orienting and positioning said loupe and lighting assembly in such a fashion as to enable enhanced detection and characterization of dust contaminants on the sensor.

The invention also relates to a method of use as in claim 20, further including step bb), occurring between step b) and step c), said step bb) consisting of abutting a said loupe and lighting assembly against said lens socket site.

BRIEF DESCRIPTION OF THE DRAWINGS

In the drawings illustrating the preferred embodiment of the invention.

DETAILED DESCRIPTION OF THE EMBODIMENT

FIGS. 1, 3-5, 7a and 7b generally show a loupe and lighting assembly for camera sensor dust detection 10, according to the present invention, used to enhance detection and characterization of particulate contaminants on a camera sensor. This loupe and lighting assembly comprises a hollow-centered cylindroid main frame body 12, comprising a battery housing 14 containing the batteries 17 needed to power the lights of the invention and covered by a sliding cover 18 with embossed notches providing a better grip and enabling easier access. Upon the main frame body 12 is also integrated a manual trigger switch 16 allowing a selective powering of the loupe and lighting assembly and thus preventing depletion of the batteries 17 when the invention is not in use, with embossed notches for a better grip. Radially and inwardly within the cylindroid main frame body 12 is fastened a smaller hollow-centered cylindroid body with a conic flange 13 (better seen on FIGS. 2, 6 and 7c) upon which are embedded a number of light-emitting diodes (LED), preferably six, which are identified by numbers 22, 22', 22", 22"', 22"" and 22""' on FIG. 3 and disposed in a peripherally, spaced apart fashion and thus creating a LED array. Each of the diodes 22, 22', 22", 22"', 22"" and 22""' is tilted with an acute angle, preferably between 30 to 45 degrees and most preferably 30 degrees.

In the preferred embodiment, the cylindrical embossed shaped body 24 is carved upon the main frame body 12 to enable installation of the loupe and lighting assembly for camera sensor dust detection 10 abuttingly against the digital camera sensor site of a digital single-lens reflex (DSLR) camera, but the latter may alternately be used in spaced register with the sensor site opening. The loupe and lighting assembly 10 could also be used to detect and characterize particulate contaminants upon the lens of any other types of cameras, for example state of the art digital cameras, or other lenses in other applications, not excluding optical microscopy, optical and digital telescopes, spectacles lenses and alike. The field of use of the loupe and lighting assembly 10 is not limited to detecting impurities upon lenses but could also extend to any planar surfaces, although it's not the main purpose intended.

Figure 1:
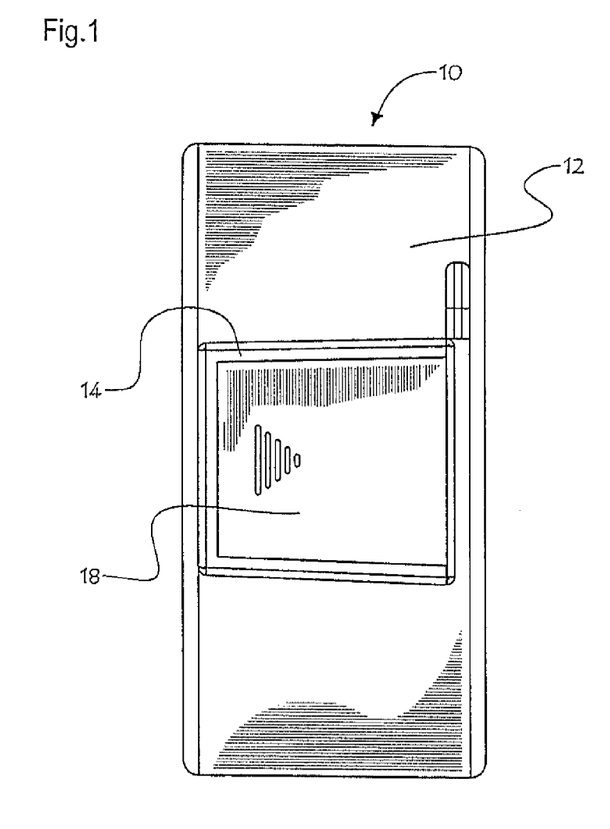
FIG. 1 is a side view of the preferred embodiment of the loupe and lighting assembly according to the present invention.
Figure 2:
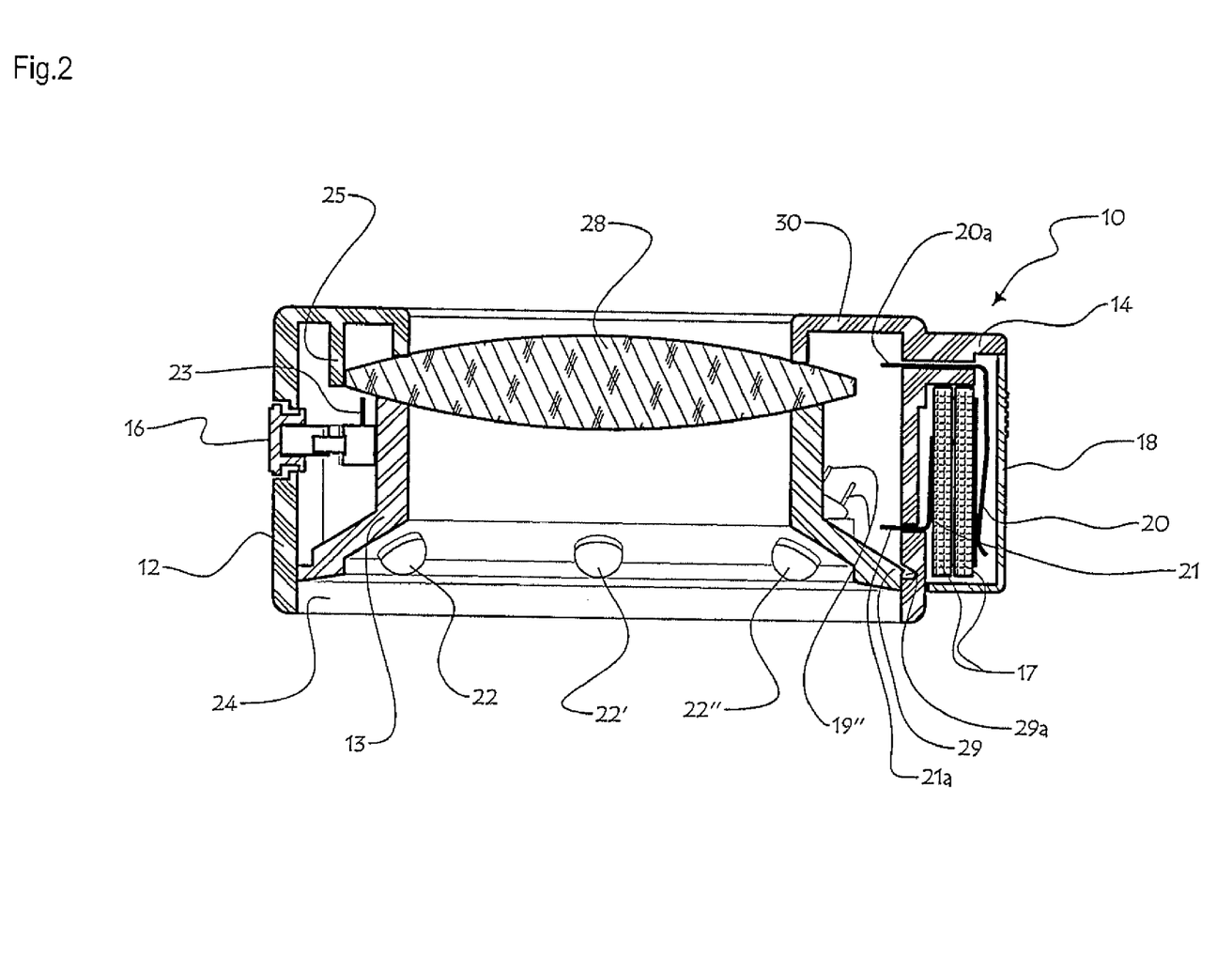
FIG. 2 shows an enlarged cross-sectional view of the preferred embodiment of FIG. 1.

As seen on FIG. 2, a radially inwardly curved rearward extension 30 of the hollow-centered cylindroid main frame body 12 is used to wedge the tapered peripheral edge of a biconvex loupe lens 28 in place against the cylindroid body with a forward conic flange 13, coplanar therewith. Both of these parts forwardly (13) and backwardly (30) wedging the loupe lens 28 therebetween have a slightly slanted edge where they make contact in order for the loupe lens 28 to frictionally interlock between them. Another transverse extension 25 of the hollow-centered cylindroid main frame body 12 extends inside the loupe and lighting assembly 10 and further constitutes an edgewise abutment stopper for loupe lens 28 to protect against accidental lateral movements thereof. A forward radially outwardly extending protuberance 29 of the hollow-centered cylindroid body with a conic flange 13 is used to fasten the latter to the main frame body 12 when said protuberance 29 is inserted into an annular notch 29a, which is carved upon the radially inward peripheral surface of the main frame body 12.

As said before, inside the battery housing 14 are preferably two discoid batteries 17. Those batteries 17 are making contact with two electrodes 20 and 21 (FIG. 2). Wires 20a and 21a of electrodes 20 and 21 project radially inwardly through the wall of the main frame body 12 and into the annular hollow between body extensions 13 and 30 and the main frame body 12. Electrodes 20 and 21 enable the flow of electric current through wires 20a and 21a. Wires 20a and 21a connect with the metallic contacts 23 of the manual trigger switch 16 and then to the electrodes 19, 19', 19", 19"', 19"" and 19""' of the corresponding LED 22, 22', 22", 22"', 22"" and 22""', making a series circuit and thus enabling the powering of the loupe and lighting assembly for camera sensor dust detection 10. A parallel circuit could also be made with the diodes, thus allowing easier detection and replacement thereafter of dead diodes, if this situation was to happen. The two batteries 17 used to power the series circuit may be CR2025 lithium batteries or preferably the more recent CR2032 Lithium batteries.

Figure 7A:
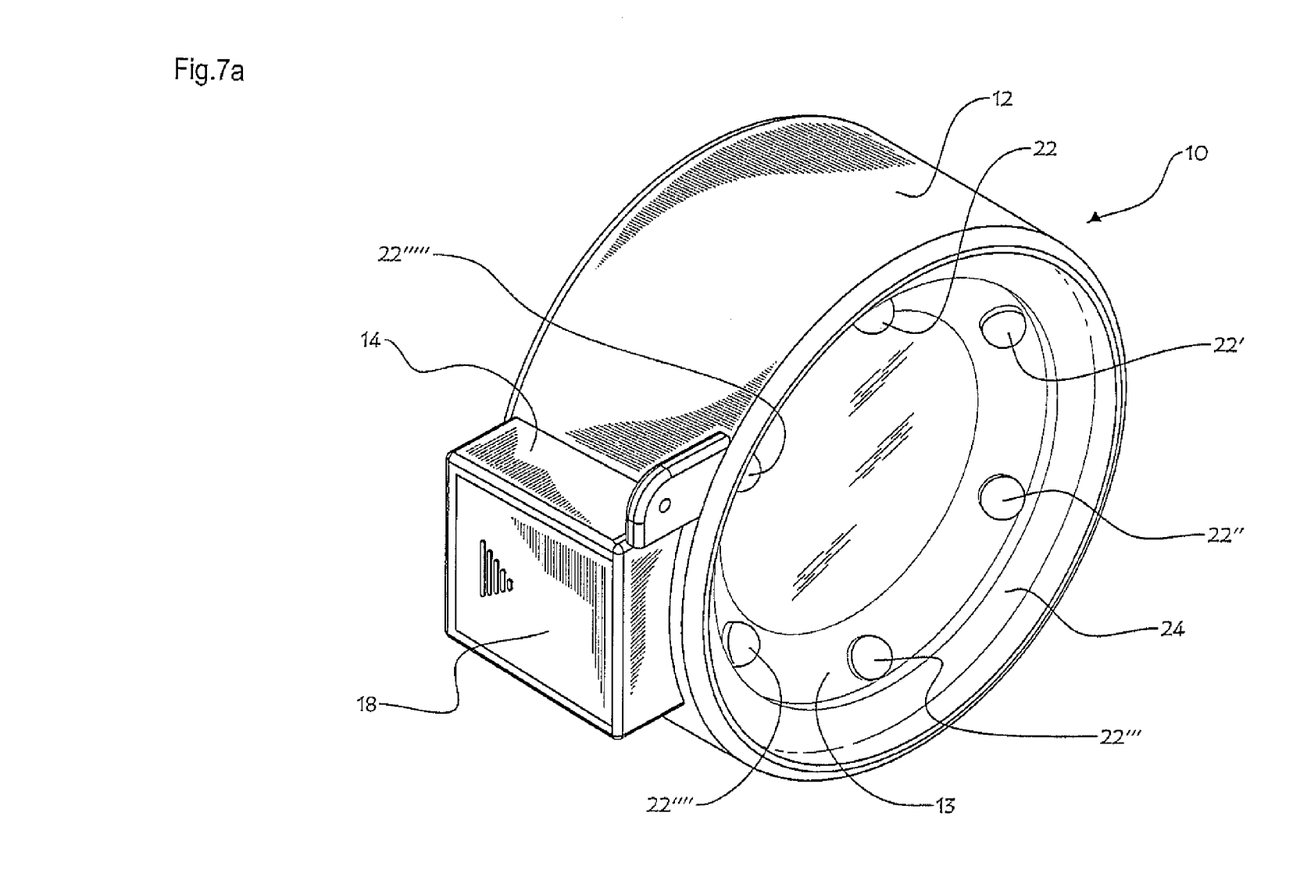
FIGS. 7a and 7b are two perspective views of the loupe and lighting assembly of FIG. 1, from two different perspectives.
Figure 7B:
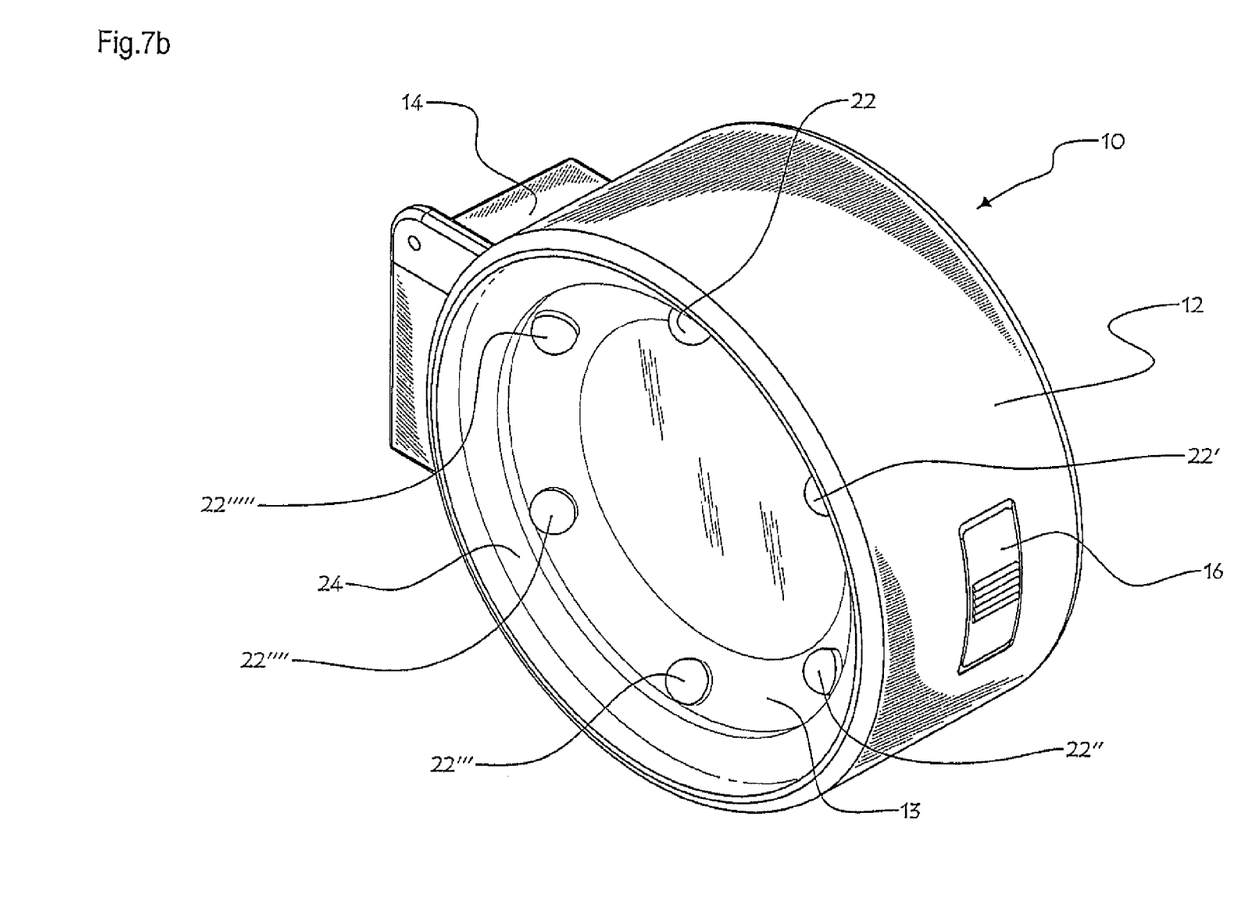
Figure 7C:
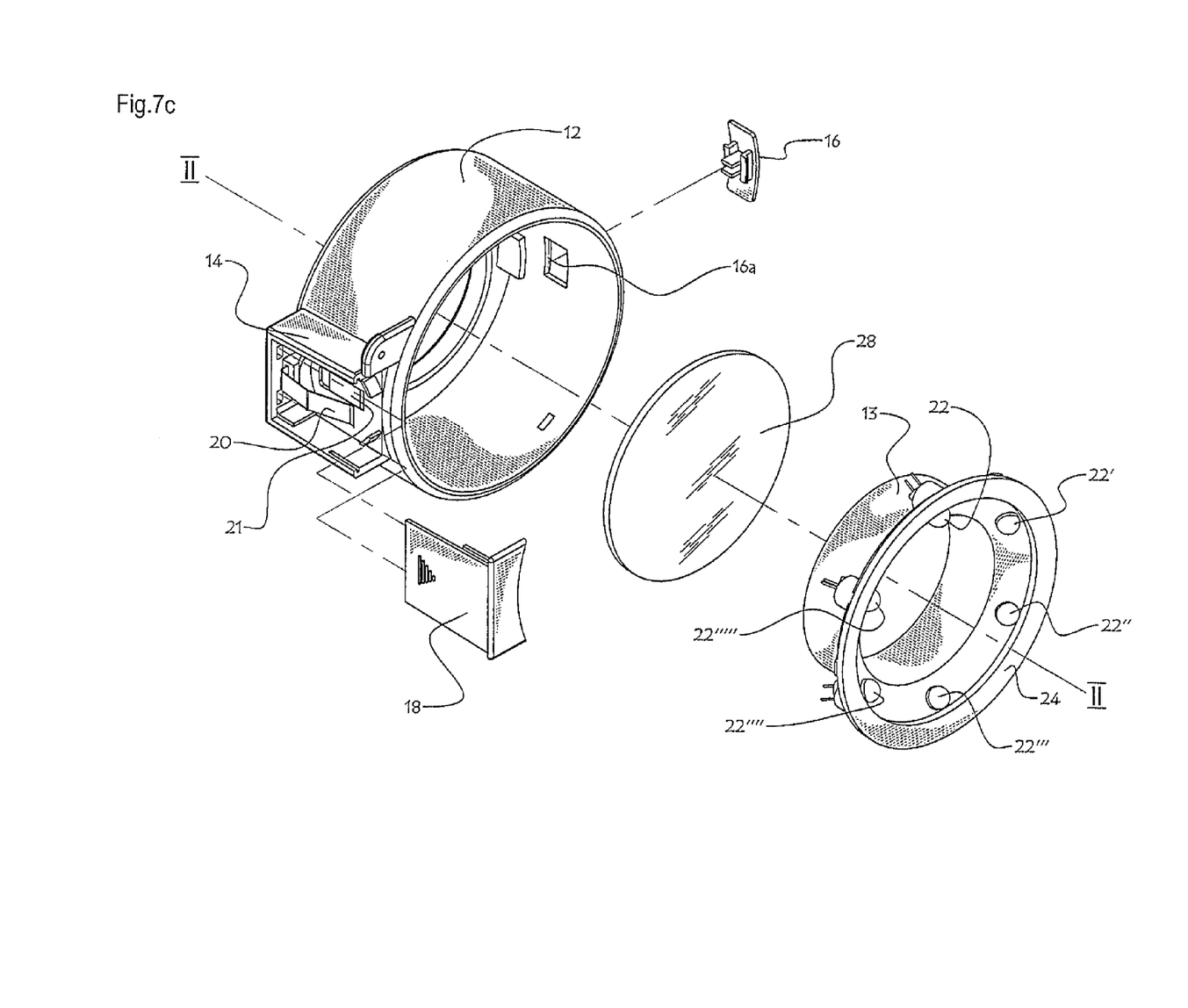
FIG. 7c is an exploded perspective view of the loupe and lighting assembly, taken from the perspective of FIG. 4.

The manual trigger switch 16 is nested within and retained into a corresponding radial orifice 16a made in main body 12 as seen on FIG. 7c which allows it to slide circumferentially tangentially along the side of the main frame body 12. The manual trigger switch 16 has a powered-off limit position, corresponding to an open circuit and no power circulating inside the loupe and lighting assembly for camera sensor dust detection 10, and a powered-on limit position, corresponding to a closed circuit and enabling the normal functioning of the loupe and lighting assembly 10.

Figure 6:
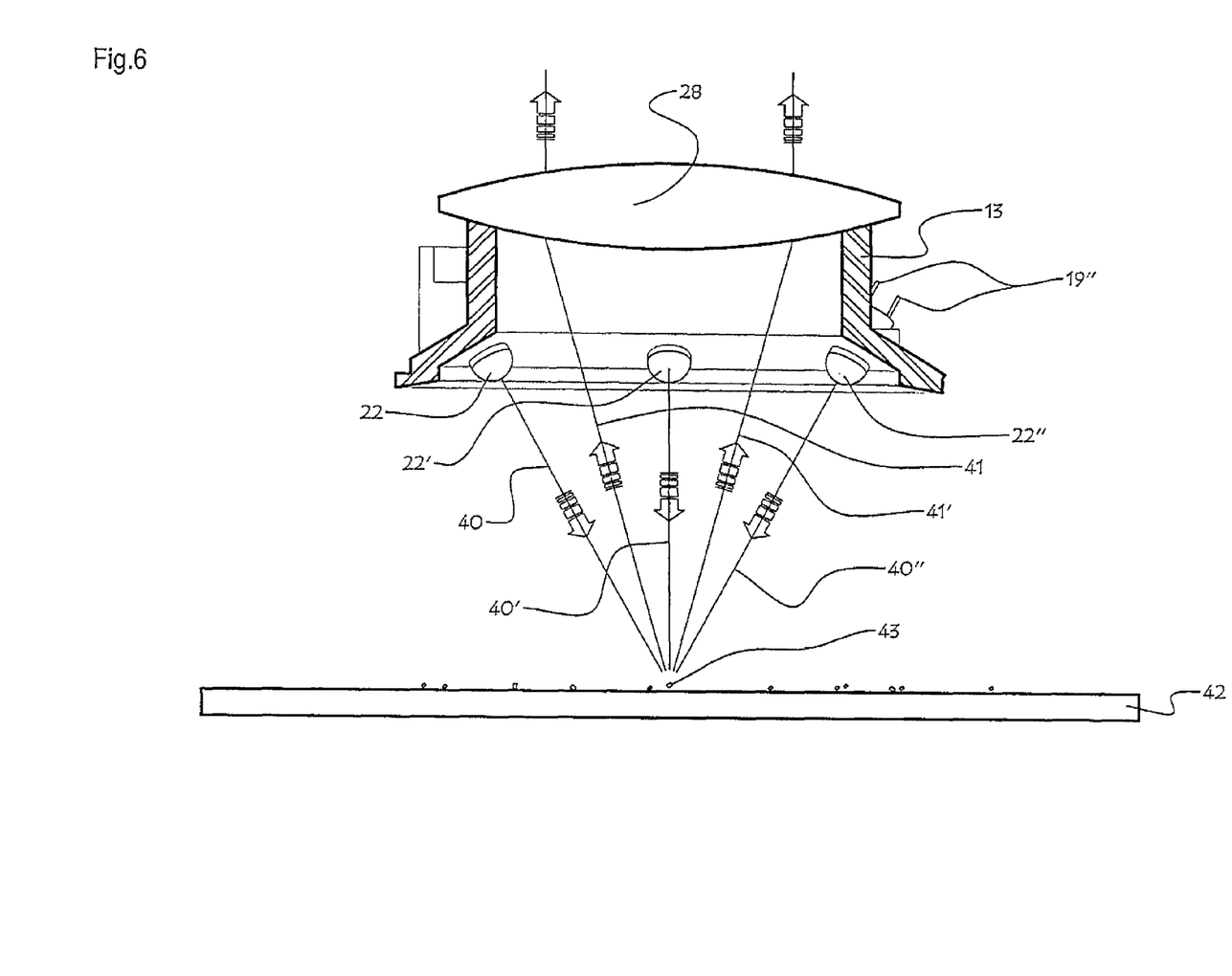
FIG. 6 is a partly broken schematic cross-sectional view similar to FIG. 2 but at a smaller scale, and further showing in edge view a planar sensor with dust particles to be detected and characterized by the present invention, the sensor at a distance from the loupe and lighting assembly.

FIG. 6 shows the light rays 40, 40' and 40" emitted by the LED array comprising diodes 22, 22', 22", 22"', 22"" and 22""' when the loupe and lighting assembly 10 is activated by displacing the manual trigger switch 16 from the powered-off limit position to the powered-on limit position. Those incident rays 40, 40' and 40" are absorbed by the dust particle 43 resting upon the sensor surface 42 and located at the focal point of both the LED array comprising diodes 22, 22' and 22" and the loupe lens 28. Reflected rays 41 and 41' are reemitted by the dust particle 43 and passing through the loupe lens 28, coming out parallel to each other so an observer looking through the loupe and lighting assembly for camera sensor dust detection 10 witnesses an enlarged image of this dust particle. The loupe lens 28 is a thick biconvex converging lens operating like a magnifying glass, i.e. enlarging an object seen through loupe lens 28 and located between the focal point of the lens and the lens itself by augmenting the apparent angle with which the observer is looking at the object, which is in this case the dust particle 43. The image thereby created is virtual and of a bigger size than the original object, thus giving the observer the impression that the object has been enlarged. When the object is located in the focal plane of the loupe lens 28, which comprises said focal point, the rays coming from the object and going through the lens are thereafter parallel to each other, creating a virtual image at infinity with a certain enlargement that is not maximum. However, in such a situation the eye lens is relaxed and thus looking at the enlarged object requires no accommodation, so the observer can stare at it for extended periods of time without tiring. The ratio of the angle subtended by the image when looking through the loupe lens 28 to the angle subtended by the object when looking at it without optical apparatus at a given distance, the "punctum proximum", is called angular magnification, or magnification power. This value allows the determination of how much bigger the object is seen when looking through the loupe lens 28. In the case of a magnifying glass like the loupe lens 28, the angular magnification simplifies to the ratio of the "punctum proximum" of the eye, which is estimated to be 25 centimeters, to the focal length of the lens.

Figure 3:
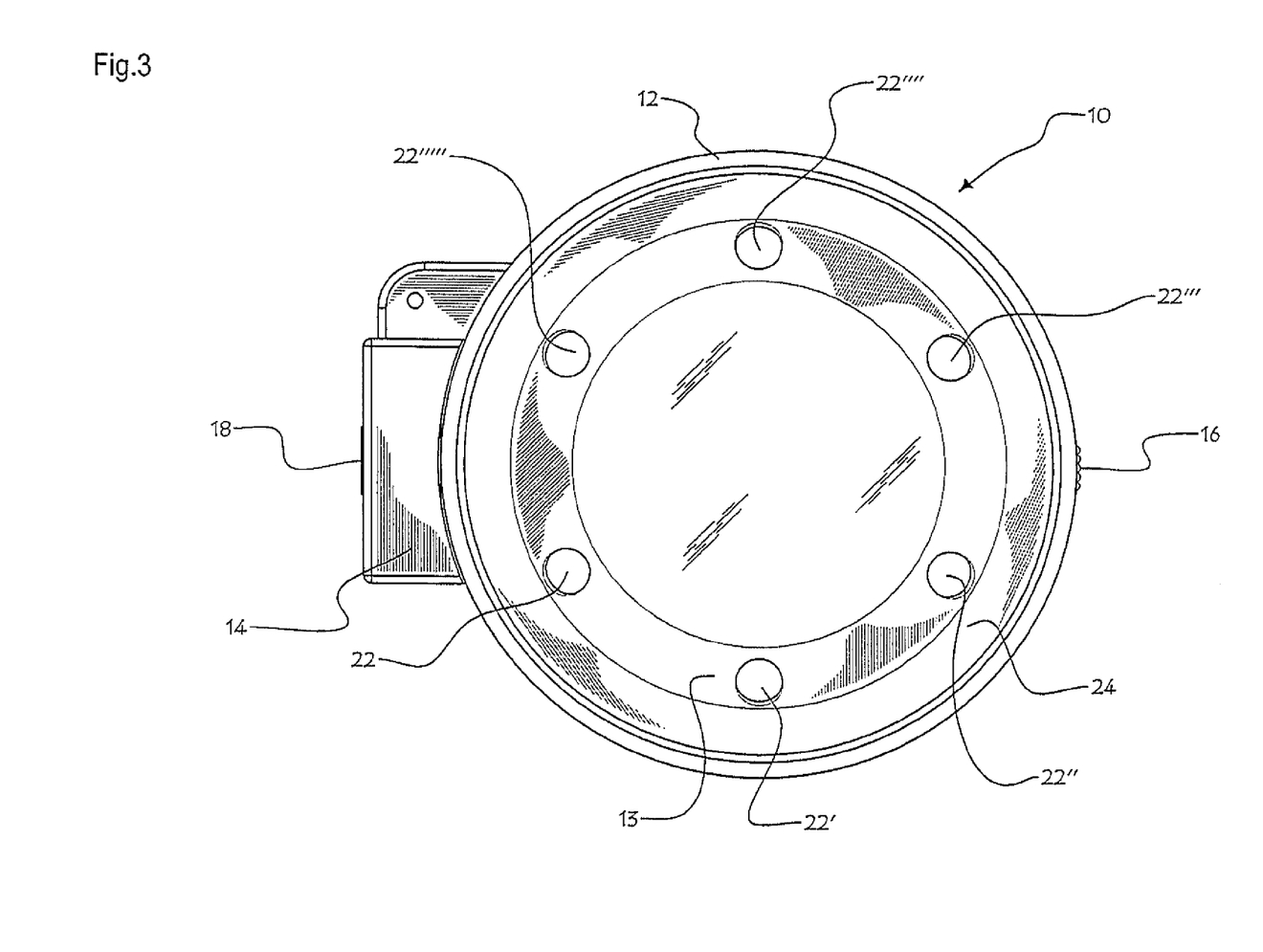
FIG. 3 is a bottom plan view of the preferred embodiment.
Figure 4:
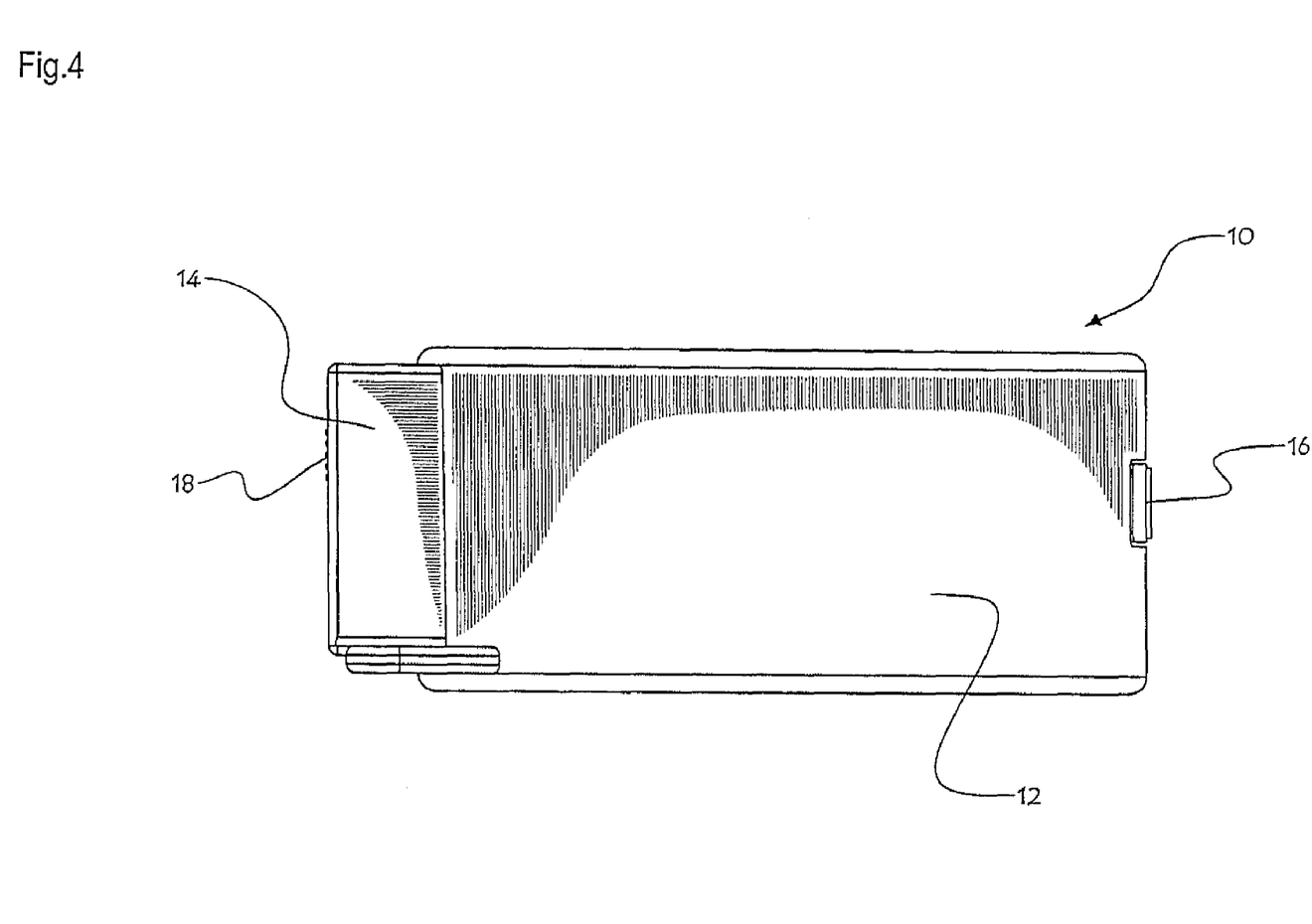
FIG. 4 is another side view of the preferred embodiment, relative to FIG. 1.
Figure 5:
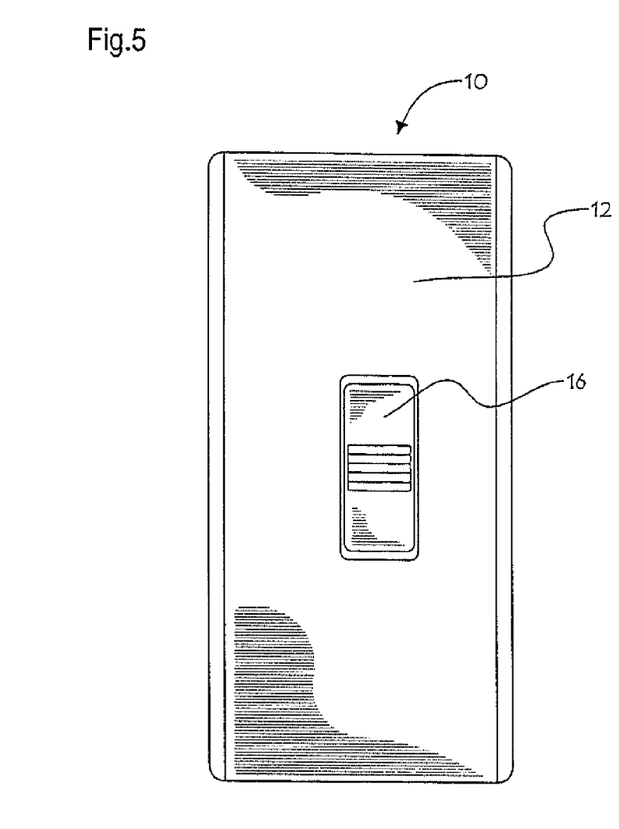
FIG. 5 on the first sheet of drawings is yet another side view of the preferred embodiment, relative to FIGS. 1 and 4.

The particular disposition of LED array 22, 22', 22", 22"', 22"" and 22""' as seen on FIG. 3, allows for a 3 dimensional effect over the particles resting on the sensor surface 42. This way of lighting the dust particle 43 gives a better contrast by casting a halo of shadow around said dust particle 43 and lighting a larger area of the particle surface, thus putting the emphasis on the particle for an onlooking observer and realizing the aforementioned effect, permitting detection and characterization (size and topographical contour) of the dust particle 43.

Rather than being coplanar to main body 12, the loupe lens 28 could alternately be tilted within loupe and lighting assembly 10 with a small acute angle about the planes of the cylindroid main frame body 12 and cylindroid body with a conic flange 13, however this would require complex adjustments for the diodes to have varied angles and orientations to make them focus at the same focal point as the loupe lens 28. That's why it is better for lens 28 to be coplanar within the cylindroid main frame body 12, in order for the device to have a certain circular symmetry around axis II as seen on FIG. 7c and thus requiring less work configuring the orientation of the diodes 22, 22', 22", 22"', 22"" and 22""' to focus about the focal point of loupe lens 28.

In the preferred embodiment, the loupe lens 28 is positioned in such a way as to make the entire sensor surface 42 visible through the loupe and lighting assembly 10. However, the bigger the magnification power is, the shorter the focal length will need to be. In order to comply with the two previous limitations, the operational range of magnification values of the loupe lens 28 comprised in the loupe and lighting assembly 10 has been found to be between 5× and 10×. The loupe lens 28 of the most preferred embodiment has an optimal magnification power between 5× and 7×, allowing a good focal length when taking into account the position of the sensor and a magnification allowing the detection and characterization of particulate contaminants upon the sensor surface. Also, the closer the focal point is to the lens, the more the lens will be curved, resulting in more spherical aberrations and thus deformation of the image seen through the loupe lens 28 for higher magnifications through a single lens, aberrations which are to be avoided.

The loupe lens 28 is preferably made of K9 optical glass and may have a diameter of about 50 millimeters, with an $MgF_2$ coating to make it anti-reflective. This coating gives the loupe and lighting assembly 10 a better efficiency by making more of the incoming light transmit through the loupe lens 28, augmenting light intensity getting to the user's eyes passively, that is without using more powerful LED diodes which would in turn necessitate more battery current. It also prevents chromatic aberrations and mildew build-up upon the surface of the lens, as well as unwanted reflections upon the loupe lens 28 surface, which would make the characterization and detection of dust particle 43 less reliable due to these reflections parasitizing the image perceived by the observer. Light-emitting diodes 22, 22', 22", 22"', 22"" and 22""' are preferably 5 millimeters wide and of water clear color, with a luminous intensity between 18000 and 20000 mcd (milli-candela). In the preferred embodiment, the main frame body 12, the smaller cylindroid body with a conic flange 13, the battery housing 14, the sliding cover 18 and the manual trigger switch 16 are made out of acrylonitrile butadiene styrene (ABS) plastic because of its qualities (rigidity, moldability, availability, toughness and low cost). Once dust particles are detected upon the sensor surface, a swab can be used to remove them without damaging the filter coating of the sensor, for example an anti-smear cleaning swab with perforated blade as disclosed in applicant's publication No. WO 2007/112550 A1 published Oct. 11, 2007.

Figure 8:
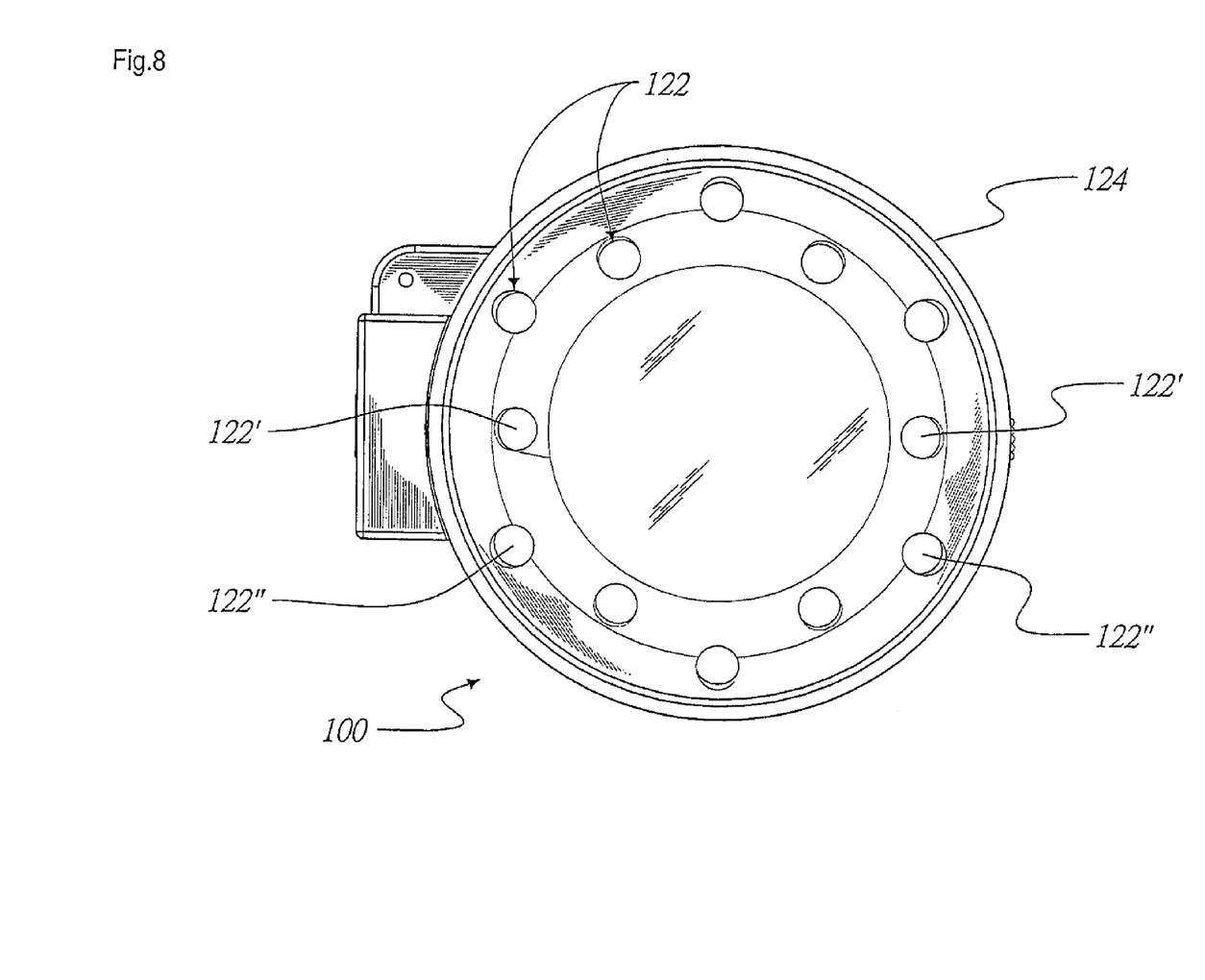
FIG. 8 is a bottom plan view of a loupe and lighting assembly according to another embodiment of the invention.
Figure 9:
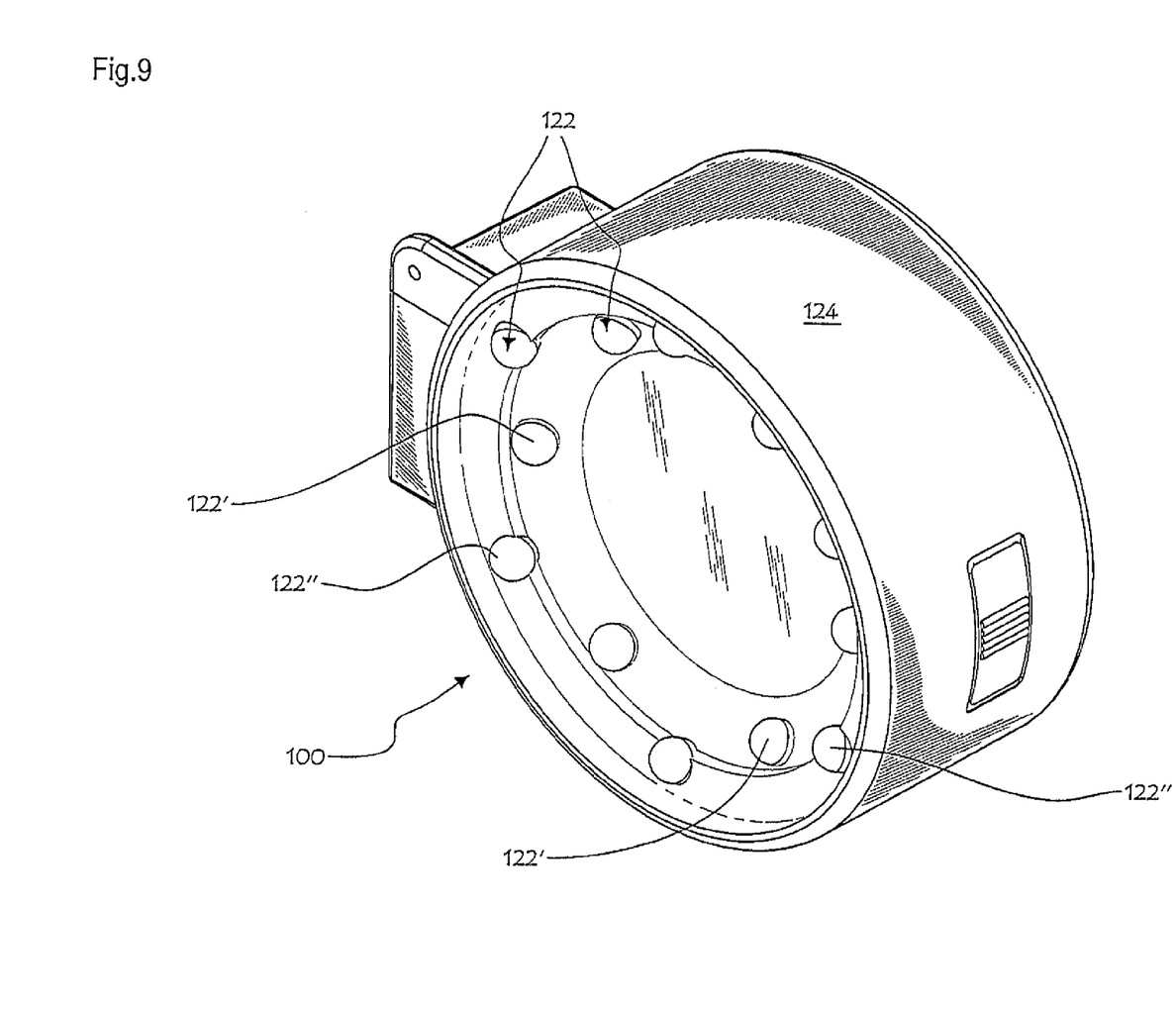
FIG. 9 is a perspective view of the loupe and lighting assembly illustrated in FIG. 8.

FIGS. 8-9 show an alternate embodiment of the loupe and lighting assembly, 100, where the LED diodes 122 are disposed in first and second transversely spaced adjacent rows 122', 122", respectively, inside the cylindroid body 124. The diodes 122' from the first row have a first acute angle, and the LED diodes 122" from the second row have a second acute angle different from the first acute angle. Preferably, the first acute angle of LED diodes 122' is about 30 degrees. Preferably also, the second acute angle of LED diodes 122" is about 45 degrees. In a preferred embodiment, each of the first row and the second row of LED diodes 122', 122", comprises six (6) LED diodes, peripherally and equidistantly disposed inside the cylindroid main frame body 124.

The invention claimed is:

1. A loupe and lighting assembly for enhancing detection of particulate contaminants on a planar surface, said assembly comprising a power source, a main frame body, light emitting means carried by said main frame body and operatively connected to said power source and a loupe lens also carried by said main frame body, said light emitting means having means for generating a 3 dimensional effect over the particulate contaminants on the planar surface, wherein enhanced detection and characterization of the particulate contaminants is achieved; wherein said light emitting means consists of a number of light emitting diodes arrayed peripherally of said main frame body; wherein said means for generating the 3 dimensional effect consists in each light emitting diode being tilted with a small acute angle from an axis extending orthogonally through a plane of said main frame body, so that said light emitting diodes are focused at a common point in space ahead of said assembly; wherein said main frame body is of cylindroid shape and said light emitting diodes are peripherally and equidistantly disposed within said cylindroid body; wherein said light emitting diodes are disposed in first and second transversely spaced adjacent rows inside said cylindroid body, said light emitting diodes from said first row having a first acute angle and said light emitting diodes from said second row having a second acute angle different from said first acute angle; and wherein said first acute angle is about 30 degrees and said second acute angle is about 45 degrees.

2. A loupe and lighting assembly for enhancing detection of particulate contaminants on a planar surface, said assembly comprising a power source, a main frame body, light emitting means carried by said main frame body and operatively connected to said power source and a loupe lens also carried by said main frame body, said light emitting means having means for generating a 3 dimensional effect over the particulate contaminants on the planar surface, wherein enhanced detection and characterization of said particulate contaminants is achieved; wherein said light emitting means consists of a number of light emitting diodes arrayed peripherally of said main frame body; wherein said means for generating the 3 dimensional effect consists in each light emitting diode being tilted with a small acute angle from an axis extending orthogonally through a plane of said main frame body, so that said light emitting diodes are focused at a common point in space ahead of said assembly; wherein said main frame body is of cylindroid shape and said light emitting diodes are peripherally and equidistantly disposed within said cylindroid body; wherein said light emitting diodes are disposed in first and second transversely adjacent rows inside said cylindroid body, said light emitting diodes from said first row having a first acute angle and said light emitting diodes from said second row having a second acute angle different from said first acute angle; and wherein each of said first row and said second row comprises 6 light emitting diodes peripherally and equidistantly disposed inside said cylindroid main frame body.

3. The loupe and lighting assembly of claim 1, wherein a bottom end of said cylindroid main frame body is shaped and sized complementarily to a digital camera site to abuttingly fit therein.

4. The loupe and lighting assembly of claim 1, wherein said light emitting diodes are of an even number.

5. The loupe and lighting assembly of claim 2, wherein said power source is an electrical battery operatively carried by said main frame body, said battery powering said loupe and lighting assembly and said main frame body comprising a sliding panel which covers said battery and insures said battery stays in place.

6. The loupe and lighting assembly of claim 2, wherein said loupe lens has a magnification capacity between 5× and 10×.

7. The loupe and lighting assembly of claim 2, wherein an electromagnetic spectrum emitted by said light emitting diodes is selected from a group comprising an ultraviolet range of wavelengths and an infrared range of wavelengths.

8. The loupe and lighting assembly of claim 2, wherein the loupe lens further includes an anti-reflective coating.

9. The loupe and lighting assembly of claim 8, wherein said anti-reflective coating is made of $MgF_2$.

10. The loupe and lighting assembly of claim 2, wherein a manual trigger switch is provided to said main frame body and operatively connected to said power source and to said light emitting means, said trigger switch enabling a user to selectively activate said loupe and lighting assembly only when required and thus preventing unnecessary use of said power source.

* * * * *